US011953512B2

(12) United States Patent
Zhang et al.

(10) Patent No.: US 11,953,512 B2
(45) Date of Patent: Apr. 9, 2024

(54) INTELLIGENT EXPERIMENTAL DEVICE FOR COLLABORATIVE MINING OF ASSOCIATED RESOURCES

(71) Applicant: ANHUI UNIVERSITY OF SCIENCE AND TECHNOLOGY, Anhui (CN)

(72) Inventors: Tong Zhang, Anhui (CN); Xiang Yu, Anhui (CN); Yankun Ma, Anhui (CN); Yanfang Li, Anhui (CN); Liang Yuan, Anhui (CN); Zegong Liu, Anhui (CN)

(73) Assignee: ANHUI UNIVERSITY OF SCIENCE AND TECHNOLOGY, Anhui (CN)

( * ) Notice: Subject to any disclaimer, the term of this patent is extended or adjusted under 35 U.S.C. 154(b) by 0 days.

(21) Appl. No.: 18/266,741

(22) PCT Filed: May 19, 2022

(86) PCT No.: PCT/CN2022/093832
§ 371 (c)(1),
(2) Date: Jun. 12, 2023

(87) PCT Pub. No.: WO2022/252997
PCT Pub. Date: Dec. 8, 2022

(65) Prior Publication Data
US 2023/0393165 A1 Dec. 7, 2023

(30) Foreign Application Priority Data
Jun. 3, 2021 (CN) .......................... 202110618111.9

(51) Int. Cl.
*G01N 35/10* (2006.01)
*G01N 33/24* (2006.01)
(Continued)

(52) U.S. Cl.
CPC ............. *G01N 35/10* (2013.01); *G01N 33/24* (2013.01); *G01N 2001/002* (2013.01); *G01N 2035/00465* (2013.01)

(58) Field of Classification Search
CPC ........ G01N 35/00; G01N 35/10; G01N 33/24; G01N 2035/00465; G01N 2001/002
See application file for complete search history.

(56) References Cited

U.S. PATENT DOCUMENTS

2015/0310951 A1 10/2015 Lu et al.
2023/0242432 A1* 8/2023 Rostro .................. C02F 11/127
210/723

FOREIGN PATENT DOCUMENTS

CN 102912147 A 2/2013
CN 106153857 A 11/2016
(Continued)

*Primary Examiner* — Nguyen Q. Ha
(74) *Attorney, Agent, or Firm* — MUNCY, GEISSLER, OLDS & LOWE, P.C.

(57) ABSTRACT

An intelligent experimental device for collaborative mining of associated resources includes a signal transmission mechanism, a pressure maintaining mechanism, a feeding mechanism, and a reaction mechanism. The signal transmission mechanism includes a centralized controller, an annunciator, signal receivers, a power supply, a power cord, signal transmitters, and signal sensing valves. The pressure maintaining mechanism includes ambient and axial pressure oil chambers, ambient and axial pressure pumps, ambient and axial pressure liquid distribution tanks, a comprehensive pressure distribution pipe, and hydraulic transmission pipes. The feeding mechanism includes monitoring analyzers, temperature controllers, solution transfer pipes, seepage pumps, mixture conveying pipes, a comprehensive liquid distributor, an aggregate chamber, a liquid chamber, an oil chamber, a gas chamber, a mixing chamber and an analytical purifier. The reaction mechanism includes a uranium mine cavity, a (Continued)

coal seam cavity, an oil-gas cavity, nuclear magnets, thermohydraulic sensors, and shearing gaskets.

4 Claims, 1 Drawing Sheet

(51) Int. Cl.
  *G01N 1/00* (2006.01)
  *G01N 35/00* (2006.01)

(56) References Cited

FOREIGN PATENT DOCUMENTS

| | | |
|---|---|---|
| CN | 106321025 A | 1/2017 |
| CN | 106337685 A | 1/2017 |
| CN | 110018057 A | 7/2019 |
| CN | 110043261 A | 7/2019 |
| CN | 110160885 A | 8/2019 |
| CN | 110208490 A | 9/2019 |
| CN | 110659782 A | 1/2020 |
| CN | 211740920 U | 10/2020 |
| CN | 110738915 A | 1/2021 |
| CN | 112727406 A | 4/2021 |

* cited by examiner

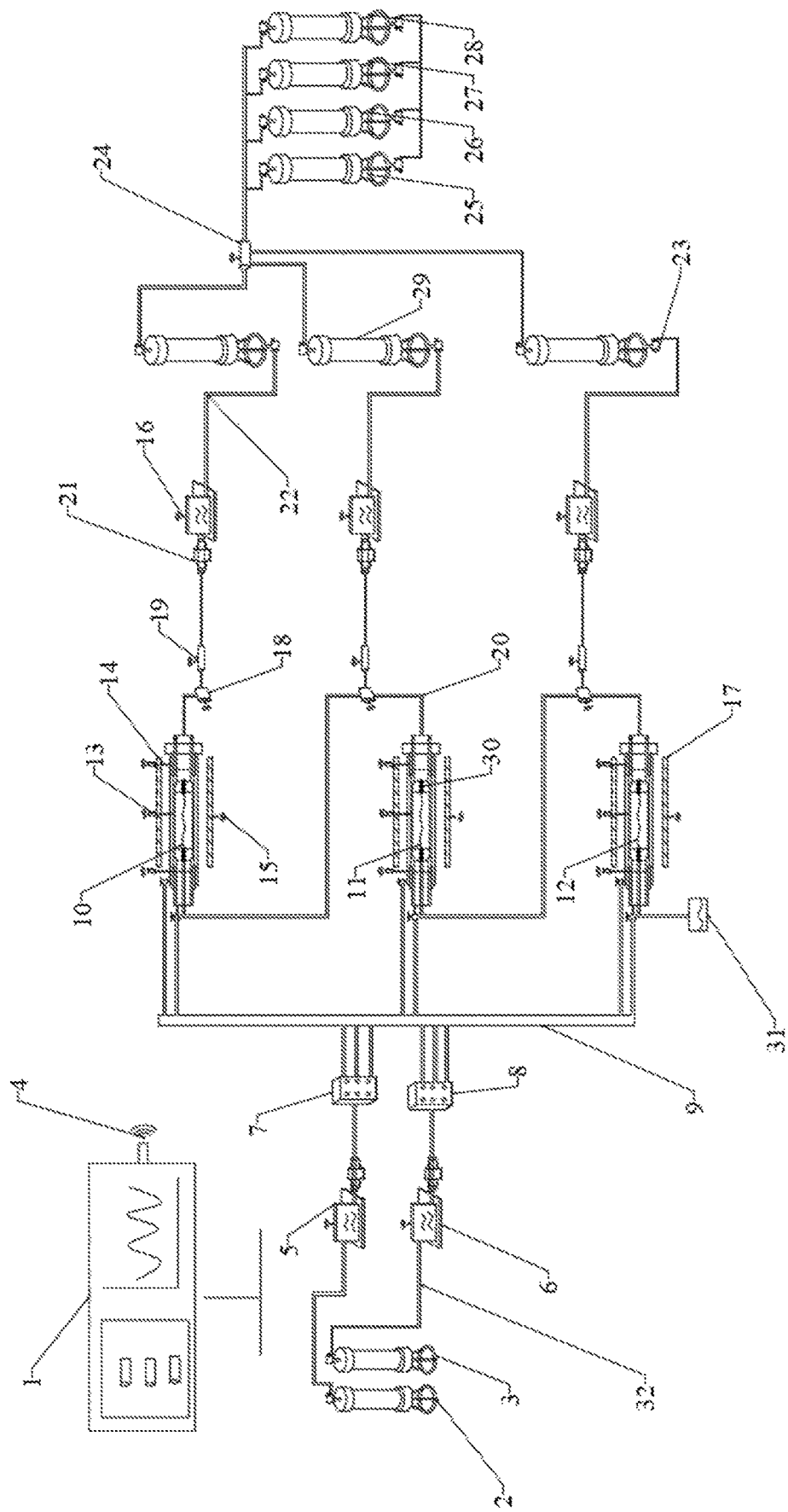

US 11,953,512 B2

INTELLIGENT EXPERIMENTAL DEVICE FOR COLLABORATIVE MINING OF ASSOCIATED RESOURCES

TECHNICAL FIELD

The present disclosure relates to the field of collaborative green mining of associated resources, in particular to an intelligent experimental device for collaborative mining of associated resources.

BACKGROUND

There are as many as 31 superimposed basins of coal and oil-gas associated resources represented by Ordos basin in the world. The distribution of associated resources presents the characteristics of "multiple points, wide area and vertical superposition". In 2019, China's fossil energy consumption accounted for 85.7%, of which coal, oil and natural gas accounted for 57.7%, 19.3% and 8.7% respectively. At the same time, the external dependence of oil and natural gas was as high as 72.5% and 43% respectively. China's energy structure as a whole is "rich in coal, poor in oil and little in gas". In future, coal will remain the dominant energy for a long time, and uranium and oil-gas are important strategic resources. The development of symbiotic superimposed resources represented by coal, uranium and oil-gas is facing the challenges of safe and efficient production and ecological environment protection. It is particularly important to study the multi-field coupling evolution characteristics of stress field, fracture field and seepage field of disturbed rock strata in the collaborative mining of coal and oil-gas. However, there are still gaps in the development of in-situ experimental devices for associated resources in universities, enterprises and research institutes at the present stage. Based on this, there is an urgently need for an intelligent experimental device for collaborative mining of associated resources to provide means support for the basic theory of safe, efficient and green development of associated resources and the research and development of key science and technology.

SUMMARY

The present disclosure aims at providing an intelligent experimental device for collaborative mining of associated resources. The intelligent experimental device for collaborative mining of associated resources includes a signal transmission mechanism, a pressure maintaining mechanism, a feeding mechanism, and a reaction mechanism. The signal transmission mechanism controls a whole mesoscopic experimental device by a transmission signal, and transmits signals to the pressure maintaining mechanism and the feeding mechanism in sequence according to experimental settings, so that three cavities of uranium, coal seam and oil-gas reach experimental preset values. The reaction system transmits data signals to a centralized controller, thereby realizing intelligently controlled collaborative mining of associated resources.

An intelligent experimental device for collaborative mining of associated resources includes:

a signal transmission mechanism including a centralized controller, an annunciator, signal receivers, a power supply, a power cord, signal transmitters, and signal sensing valves, a pressure maintaining mechanism including an ambient pressure oil chamber, an axial pressure oil chamber, an ambient pressure pump, an axial pressure pump, an ambient pressure liquid distribution tank, an axial pressure liquid distribution tank, a comprehensive pressure distribution pipe, and hydraulic transmission pipes, a feeding mechanism including monitoring analyzers, temperature controllers, solution transfer pipes, seepage pumps, mixture conveying pipes, a comprehensive liquid distributor, an aggregate chamber, a liquid chamber, an oil chamber, a gas chamber, mixing chambers and an analytical purifier, and a reaction mechanism including a uranium mine cavity, a coal seam cavity, an oil-gas cavity, nuclear magnets, thermohydraulic sensors, and shearing gaskets, where the annunciator is arranged in the centralized controller, the signal receiver is arranged in the axial pressure pump, the ambient pressure pump, the temperature controller, the seepage pump and the comprehensive liquid distributor, the signal transmitter is arranged in the thermohydraulic sensor, the nuclear magnet, and the monitoring analyzer, the signal sensing valves are arranged at the bottoms of the ambient pressure oil chamber, the axial pressure oil chamber, the aggregate chamber, the liquid chamber, the oil chamber, the gas chamber, and the mixing chamber, the ambient pressure oil chamber and the axial pressure oil chamber are respectively and directly connected to the ambient pressure pump and the axial pressure pump through the hydraulic transmission pipes, the two ends of the ambient pressure liquid distribution tank are respectively connected to the ambient pressure pump and the comprehensive pressure distribution pipe, the two ends of the axial pressure liquid distribution tank are respectively connected to the axial pressure pump and the comprehensive pressure distribution pipe, one end of the monitoring analyzer is connected to the temperature controller, one end of the seepage pump is connected to the temperature controller, the other end of the seepage pump is connected to the mixing chamber through the mixture conveying pipe, the front end of the comprehensive liquid distributor is connected to the mixing chamber through the mixture conveying pipe, the rear end of the comprehensive liquid distributor is connected to the aggregate chamber, the liquid chamber, the oil chamber, and the gas chamber respectively through the mixture conveying pipes, the analytical purifier is connected to an outlet end of the oil-gas cavity, the uranium mine cavity, the coal seam cavity, and the oil-gas cavity are connected in series through the solution transfer pipes, one ends of the uranium mine cavity, the coal seam cavity, and the oil-gas cavity are directly connected to the comprehensive pressure distribution pipe, the other ends of the uranium mine cavity, the coal seam cavity, and the oil-gas cavity are directly connected to the monitoring analyzer, the outer sides of the uranium mine cavity, the coal seam cavity, and the oil-gas cavity are wrapped with the nuclear magnets, the shearing gaskets are arranged inside the cavities, the signal transmitter is installed on the nuclear magnet, and the thermohydraulic sensors are installed at the front, middle and back positions of the uranium mine cavity, the coal seam cavity and the oil-gas cavity, and are externally connected to the signal transmitters.

Preferably, the comprehensive pressure distribution pipe is a pressure distribution device, the front side of the comprehensive pressure distribution pipe is directly connected to the ambient pressure liquid distribution tank and the axial pressure liquid distribution tank, and the rear side of the comprehensive pressure distribution pipe is directly connected to the uranium mine cavity, the coal seam cavity and the oil-gas cavity.

Preferably, the outer side of the uranium mine cavity is wrapped with the nuclear magnet, the shearing gasket is arranged inside the cavity, the thermohydraulic sensors are installed at the front, middle and back positions of the cavity, and are externally connected to the signal transmitter.

Preferably, the front end of the monitoring analyzer is connected to the uranium mine cavity, the coal seam cavity and the oil-gas cavity, and the back end of the monitoring analyzer is directly connected to the temperature controller.

Preferably, the front end of the comprehensive liquid distributor is connected to the mixing chamber through the mixture conveying pipe, and the rear end of the comprehensive liquid distributor is connected to the aggregate chamber, the liquid chamber, the oil chamber and the gas chamber through conveying pipelines respectively.

Compared with a traditional experimental device, the intelligent experimental device for collaborative mining of associated resources provided by the present disclosure has the following advantages: the intelligent experimental device includes a signal transmission mechanism, a pressure maintaining mechanism, a feeding mechanism, and a reaction mechanism; the signal transmission mechanism controls a whole mesoscopic experimental device by a transmission signal, and transmits signals to the pressure maintaining mechanism and the feeding mechanism in sequence according to experimental settings, so that three cavities of uranium, coal seam and oil-gas reach experimental preset values; and the reaction system transmits data signals to the centralized controller, thereby realizing intelligently controlled collaborative mining of associated resources. The comprehensive pressure distribution pipe can evenly distribute the axial pressure and the ambient pressure to the uranium mine cavity, the coal seam cavity and the oil-gas cavity according to the preset values; the gaskets in the cavities are shearing gaskets, which can shear an internal rock mass under a true triaxial condition; the monitoring analyzer can monitor the temperature, pressure and composition, and transmits a feedback signal to the centralized controller through the installed signal transmitter; and the comprehensive liquid distributor can realize the even distribution of the experimental mixture and distributes the mixture into the corresponding mixing chamber.

BRIEF DESCRIPTION OF THE DRAWINGS

The FIGURE is a mechanism system diagram of an intelligent experimental device for collaborative mining of associated resources.

In the figure, 1—centralized controller; 2—ambient pressure oil chamber; 3—axial pressure oil chamber; 4—annunciator; 5—ambient pressure pump; 6—axial pressure pump; 7—ambient pressure liquid distribution tank; 8—axial pressure liquid distribution tank; 9—comprehensive pressure distribution pipe; 10—uranium mine cavity; 11—coal seam cavity; 12—oil-gas cavity; 13—signal transmitter; 14—thermohydraulic sensor; 15—signal transmitter; 16—signal receiver; 17—nuclear magnet; 18—monitoring analyzer; 19—temperature controller; 20—solution transfer pipe; 21—seepage pump; 22—mixture conveying pipe; 23—signal sensing valve; 24—comprehensive liquid distributor; 25—aggregate chamber; 26—liquid chamber; 27—oil chamber; 28—gas chamber; 29—mixing chamber; 30—shearing gasket; 31—analytical purifier; 32—hydraulic transmission pipe.

DETAILED DESCRIPTION

As shown in conjunction with the Figure, an intelligent experimental device for collaborative mining of associated resources includes a signal transmission mechanism, a pressure maintaining mechanism, a feeding mechanism, and a reaction mechanism. The signal transmission mechanism controls a whole mesoscopic experimental device by a transmission signal, and transmits signals to the pressure maintaining mechanism and the feeding mechanism in sequence according to experimental settings, so that three cavities of uranium, coal seam and oil-gas reach experimental preset values. The reaction system transmits data signals to a centralized controller, thereby realizing intelligently controlled collaborative mining of associated resources.

In the signal transmission mechanism, an annunciator 4 is arranged in a centralized controller 1, a signal receiver 16 is arranged in an axial pressure pump 6, an ambient pressure pump 5, a temperature controller 19, a seepage pump 21 and a comprehensive liquid distributor 24; a signal transmitter 13 is arranged in a thermohydraulic sensor 14, a nuclear magnet 17, and a monitoring analyzer 18; and signal sensing valves 23 are arranged at the bottoms of an ambient pressure oil chamber 2, an axial pressure oil chamber 3, an aggregate chamber 25, a liquid chamber 26, an oil chamber 27, a gas chamber 28, and a mixing chamber 29.

In the pressure maintaining mechanism, the ambient pressure oil chamber 2 and the axial pressure oil chamber 3 are respectively and directly connected to the ambient pressure pump 5 and the axial pressure pump 6 through hydraulic transmission pipes 32, the two ends of an ambient pressure liquid distribution tank 7 are respectively connected to the ambient pressure pump 5 and a comprehensive pressure distribution pipe 9, and the two ends of an axial pressure liquid distribution tank 8 are respectively connected to the axial pressure pump 6 and the comprehensive pressure distribution pipe 9.

In the feeding mechanism, one end of a monitoring analyzer 18 is connected to the temperature controller 19, one end of the seepage pump 21 is connected to the temperature controller 19, the other end of the seepage pump is connected to the mixing chamber 29 through a mixture conveying pipe 22, the front end of the comprehensive liquid distributor 24 is connected to the mixing chamber 29 through the mixture conveying pipe 22, the rear end of the comprehensive liquid distributor is connected to the aggregate chamber 25, the liquid chamber 26, the oil chamber 27, and the gas chamber 28 respectively through the mixture conveying pipes 22, and the analytical purifier 31 is connected to an outlet end of an oil-gas cavity 12.

In the reaction mechanism, a uranium mine cavity 10, a coal seam cavity 11, and the oil-gas cavity 12 are connected in series through solution transfer pipes 20, one ends of the uranium mine cavity, the coal seam cavity, and the oil-gas cavity are directly connected to the comprehensive pressure distribution pipe 9, the other ends of the uranium mine cavity, the coal seam cavity, and the oil-gas cavity are directly connected to the monitoring analyzer 18, the outer sides of the uranium mine cavity, the coal seam cavity, and the oil-gas cavity are wrapped with the nuclear magnets 17, shearing gaskets 30 are arranged inside the cavities, the signal transmitter 13 is installed on the nuclear magnet 17, and a thermohydraulic sensors 14 are installed at the front, middle and back positions of the uranium mine cavity 10, the coal seam cavity 11 and the oil-gas cavity 12, and are externally connected to the signal transmitters 13.

As shown in conjunction with the FIG. 1, the above experimental device is applied, which includes the following experimental steps:

a: according to experimental requirements, uranium mine rock samples, coal mine rock samples and oil-gas rock samples are respectively installed into the uranium mine cavity 10, the coal seam cavity 11 and the oil-gas cavity 12;

b: all parts are orderly assembled according to spatial positions and connection modes corresponding to all the parts;

c: the connection and working conditions of all the parts are checked, and experimental parameter values are input into the centralized controller 1 according to the experimental scheme under the condition of ensuring the normal work of all the parts;

d: the centralized controller 1 transmits signals to the pressure maintaining mechanism, the ambient pressure pump 5 and the axial pressure pump 6 receive the signals and are started, the signal sensing valves 23 under the ambient pressure oil chamber 2 and the axial pressure oil chamber 3 receive the signals and are started, so that ambient pressure oil and axial pressure oil are injected into the comprehensive pressure distribution pipe 9 through the ambient pressure liquid distribution tank 7 and the axial pressure liquid distribution tank 8;

e: the comprehensive pressure distribution pipe 9 injects the ambient pressure oil and the axial pressure oil into the uranium mine cavity 10, the coal seam cavity 11 and the oil-gas cavity 12 according to preset values, and after the ambient pressure and the axial pressure in the cavities reach the preset values, the thermohydraulic sensors 14 transmit signals to the centralized controller 1 through the signal transmitters 13, and the ambient pressure and the axial pressure start to keep unchanged;

f: subsequently, the centralized controller 1 transmits signals to the feeding mechanism, the signal sensing valves 23 and the signal receivers 16 receive the signals, at this time, the aggregate chamber 25, the liquid chamber 26, the oil chamber 27 and the gas chamber 28 are started, and begin to supply materials, and the materials are injected into the mixing chambers 29 through the comprehensive liquid distributor 24;

g: after the seepage pump 21 receives a signal and is started, the seepage pump injects a mixture in the mixing chamber 29 into the uranium mine cavity 10 through the mixture conveying pipe 22, the temperature controller 19 and the monitoring analyzer 18, if the temperature needs to be applied, the temperature of the temperature controller 19 can be preset, and the monitoring analyzer 18 analyzes the mixture;

h: if the composition of the mixture does not meet the experimental requirements, the monitoring analyzer 18 may transmit a feedback signal to the centralized controller 1, and then the centralized controller 1 transmits a signal to the feeding mechanism for readjustment, and steps f and g are repeated;

i: the mixture first passes through the uranium mine cavity 10, then flows into the coal seam cavity 11 and the oil-gas cavity 12 through series pipelines connected by the solution transfer pipes 20, and the coal seam cavity 11 and the oil-gas cavity 12 are also externally provided with the monitoring analyzers 18;

j: if the composition of a certain level of mixture does not meet the experimental requirements, the signal transmitter 13 on the monitoring analyzer 18 transmits a signal to the centralized controller 1, and then the centralized controller 1 transmits a signal to the seepage pump 21, the mixture is replenished from the mixing chamber 29, and steps f and g are repeated;

k: the mixture finally flows into the analytical purifier 31, and the content of each component of the mixture is analyzed by the analytical purifier 31, so as to realize purification and environment protection; and l: after the experiment is completed, a uranium mine rock mass, a coal seam rock mass and an oil-gas rock mass are taken out, and all devices are closed and cleaned up.

By all means, the above description only describes preferred examples of the present disclosure; the present disclosure is not limited to the above-mentioned examples; and it should be noted that all equivalent substitutions and obvious variations made by a person skilled in the art under the guidance of this specification fall within the essential scope of this specification and should be protected by the present disclosure.

What is claimed is:

1. An intelligent experimental device for collaborative mining of associated resources, comprising:

a signal transmission mechanism comprising a centralized controller, an annunciator, signal receivers, a power supply, a power cord, signal transmitters, and signal sensing valves, a pressure maintaining mechanism comprising an ambient pressure oil chamber, an axial pressure oil chamber, an ambient pressure pump, an axial pressure pump, an ambient pressure liquid distribution tank, an axial pressure liquid distribution tank, a comprehensive pressure distribution pipe, and hydraulic transmission pipes, a feeding mechanism comprising monitoring analyzers, temperature controllers, solution transfer pipes, seepage pumps, mixture conveying pipes, a comprehensive liquid distributor, an aggregate chamber, a liquid chamber, an oil chamber, a gas chamber, mixing chambers and an analytical purifier, and a reaction mechanism comprising a uranium mine cavity, a coal seam cavity, an oil-gas cavity, nuclear magnets, temperature hydraulic sensors, and shearing gaskets, wherein the annunciator is arranged in the centralized controller, the signal receiver is arranged in the axial pressure pump, the ambient pressure pump, the temperature controller, the seepage pump and the comprehensive liquid distributor, the signal transmitter is arranged in the temperature hydraulic sensor, the nuclear magnet, and the monitoring analyzer, the signal sensing valves are arranged at the bottoms of the ambient pressure oil chamber, the axial pressure oil chamber, the aggregate chamber, the liquid chamber, the oil chamber, the gas chamber, the mixing chamber, the ambient pressure oil chamber and the axial pressure oil chamber are respectively and directly connected to the ambient pressure pump and the axial pressure pump through the hydraulic transmission pipes, the two ends of the ambient pressure liquid distribution tank are respectively connected to the ambient pressure pump and the comprehensive pressure distribution pipe, the two ends of the axial pressure liquid distribution tank are respectively connected to the axial pressure pump and the comprehensive pressure distribution pipe, one end of the monitoring analyzer is connected to the temperature controller, one end of the seepage pump is connected to the temperature controller, while the other end of the seepage pump is connected to the mixing chamber through the mixture conveying pipe, the front end of the comprehensive liquid distributor is connected to the mixing chamber through the mixture conveying pipe, while the rear end of the comprehensive liquid distributor is connected to the aggregate chamber, the liquid chamber, the oil chamber, and the gas chamber respectively through the mixture conveying pipes, the analytical purifier is connected to an outlet end of the oil-gas cavity, the uranium mine cavity, the coal seam cavity, and the oil-gas cavity which are connected in series through the solution transfer pipes, one ends of the uranium mine cavity, the coal seam cavity, and the oil-gas cavity are directly connected to the comprehensive pressure distribution pipe, while the other ends of the uranium mine cavity, the coal seam cavity, and the oil-gas cavity are directly connected to the monitoring analyzer, the outer sides of the uranium mine cavity, the coal seam cavity, and the oil-gas cavity are wrapped with the nuclear magnets, the shearing gaskets are arranged inside the cavities, a signal transmitter is installed on the nuclear magnet, and the temperature hydraulic sensors are installed on the side walls of the uranium mine cavity, the coal seam cavity and the oil-gas cavity, and each cavity is respectively provided with a thermohydraulic sensor at the front, middle and back positions, which is externally connected to the signal transmitter.

2. The intelligent experimental device for collaborative mining of associated resources according to claim 1, wherein the comprehensive pressure distribution pipe is a pressure distribution device, the front side of the comprehensive pressure distribution pipe is directly connected to the ambient pressure liquid distribution tank and the axial pressure liquid distribution tank, while the rear side of the comprehensive pressure distribution pipe is directly connected to the uranium mine cavity, the coal seam cavity and the oil-gas cavity.

3. The intelligent experimental device for collaborative mining of associated resources according to claim 1, wherein the front end of the monitoring analyzer is connected to the uranium mine cavity, the coal seam cavity and the oil-gas cavity, while the back end of the monitoring analyzer is directly connected to the temperature controller.

4. The intelligent experimental device for collaborative mining of associated resources according to claim 1, wherein the front end of the comprehensive liquid distributor is connected to the mixing chamber through the mixture conveying pipe, while the rear end of the comprehensive liquid distributor is connected to the aggregate chamber, the liquid chamber, the oil chamber, and the gas chamber through conveying pipelines respectively.

\* \* \* \* \*